United States Patent [19]
Williamson, IV et al.

[11] Patent Number: 5,807,393
[45] Date of Patent: Sep. 15, 1998

[54] SURGICAL TISSUE TREATING DEVICE WITH LOCKING MECHANISM

[75] Inventors: Warren P. Williamson, IV, Loveland; David C. Yates, West Chester, both of Ohio

[73] Assignee: Ethicon Endo-Surgery, Inc., Cincinnati, Ohio

[21] Appl. No.: 437,262

[22] Filed: May 8, 1995

Related U.S. Application Data

[63] Continuation-in-part of Ser. No. 362,070, Dec. 22, 1992, abandoned, which is a continuation-in-part of Ser. No. 311,297, Sep. 23, 1994, Pat. No. 5,558,671, which is a continuation-in-part of Ser. No. 95,797, Jul. 22, 1993, Pat. No. 5,403,312.

[51] Int. Cl.$^6$ .................................................. A61B 17/00
[52] U.S. Cl. ............................... 606/32; 606/33; 606/41; 606/40
[58] Field of Search .................... 606/326, 37–42, 606/45–52, 120, 167; 128/642; 607/100–102, 115, 116

[56] References Cited

U.S. PATENT DOCUMENTS

| | | | |
|---|---|---|---|
| 2,031,682 | 2/1936 | Wappler et al. | 174/89 |
| 4,608,981 | 9/1986 | Rothfuss et al. | 128/305 |
| 4,633,874 | 1/1987 | Chow et al. | 128/344 R |
| 4,651,280 | 3/1987 | Chang et al. | 364/413 |
| 4,655,216 | 4/1987 | Tischer | 128/303.17 |
| 4,671,274 | 6/1987 | Sorochenko | 128/303.14 |
| 4,685,459 | 8/1987 | Koch et al. | 128/303.17 |
| 4,938,215 | 7/1990 | Schulman et al. | 606/120 |
| 4,961,047 | 10/1990 | Carder | 323/322 |
| 4,985,030 | 1/1991 | Melzer et al. | 606/51 |
| 5,057,107 | 10/1991 | Parins et al. | 606/48 |
| 5,085,659 | 2/1992 | Rydell | 606/47 |
| 5,104,025 | 4/1992 | Main et al. | 227/175 |
| 5,151,102 | 9/1992 | Kamiyama et al. | 606/51 |
| 5,167,658 | 12/1992 | Ensslin | 606/34 |

(List continued on next page.)

FOREIGN PATENT DOCUMENTS

| | | |
|---|---|---|
| 0 517 244 | 12/1992 | European Pat. Off. . |
| 0 518 230 | 12/1992 | European Pat. Off. . |
| 39 42 998 A1 | 7/1991 | Germany . |
| 2 213 381 | 8/1989 | United Kingdom . |
| WO 93/08754 | 5/1993 | WIPO . |
| WO 93/13718 | 7/1993 | WIPO . |
| WO 94/24949 | 11/1994 | WIPO . |
| WO 94/24951 | 11/1994 | WIPO . |

OTHER PUBLICATIONS

Copy of European Search Report dated Mar. 6, 1997.

Automatically Controlled Bipolar Electrocoagulation– "COA–COMP", Neurosurg. Ref. (1984) 187–190; B. Vallofors and B. Bergdahl.

Radio Frequency Energy and Impedance Feedback, SPIE vol. 1068 Catheter–Based Sensing and Imaging Technology (1989), Nardella, P.

Instrument for Stomach Resection and Bowel Anastomosis Used During Closed Procedures, Department of Surgery of Mukachevo City Hospital, N.G. Vittenberger, Jan.–Feb. 1958, First Issue (the 211th).

*Primary Examiner*—Jennifer Bahr
*Assistant Examiner*—Stephen Huang

[57] ABSTRACT

A locking mechanism for ensuring proper sequential usage of a surgical instrument is provided for an instrument utilizing a tissue treating energy, particularly a tissue heating energy, such as, for example, electrosurgical, ultrasonic, thermal, laser, infrared light, or other heating energies. One embodiment includes a cutting element to be used after heat treatment of tissue is completed to a desired degree. The instrument of the preferred embodiment includes a feedback monitor arranged to provide a signal indicating completion of tissue treatment. One embodiment includes an electromechanical locking mechanism responsive to the tissue treatment complete feedback signal and arranged to unlock when tissue treatment is complete.

16 Claims, 16 Drawing Sheets

U.S. PATENT DOCUMENTS

| | | | |
|---|---|---|---|
| 5,190,517 | 3/1993 | Zieve et al. | 604/22 |
| 5,190,541 | 3/1993 | Abele et al. | 606/46 |
| 5,201,900 | 4/1993 | Nardella | 606/157 |
| 5,207,691 | 5/1993 | Nardella | 606/142 |
| 5,290,286 | 3/1994 | Parins | 606/50 |
| 5,300,070 | 4/1994 | Gentelia et al. | 606/45 |
| 5,307,976 | 5/1994 | Olson et al. | 227/178 |
| 5,335,668 | 8/1994 | Nardella | 128/734 |
| 5,389,098 | 2/1995 | Tsuruta et al. | 606/41 |
| 5,403,312 | 4/1995 | Yates et al. | 606/50 |
| 5,417,687 | 5/1995 | Nardella et al. | 606/32 |
| 5,423,809 | 6/1995 | Klicek | 606/38 |
| 5,429,636 | 7/1995 | Shikhman et al. | 606/41 |
| 5,462,555 | 10/1995 | Bolanos et al. | 606/120 |
| 5,496,341 | 3/1996 | Sauer et al. | 606/167 |
| 5,520,699 | 5/1996 | Hessel et al. | 606/120 |

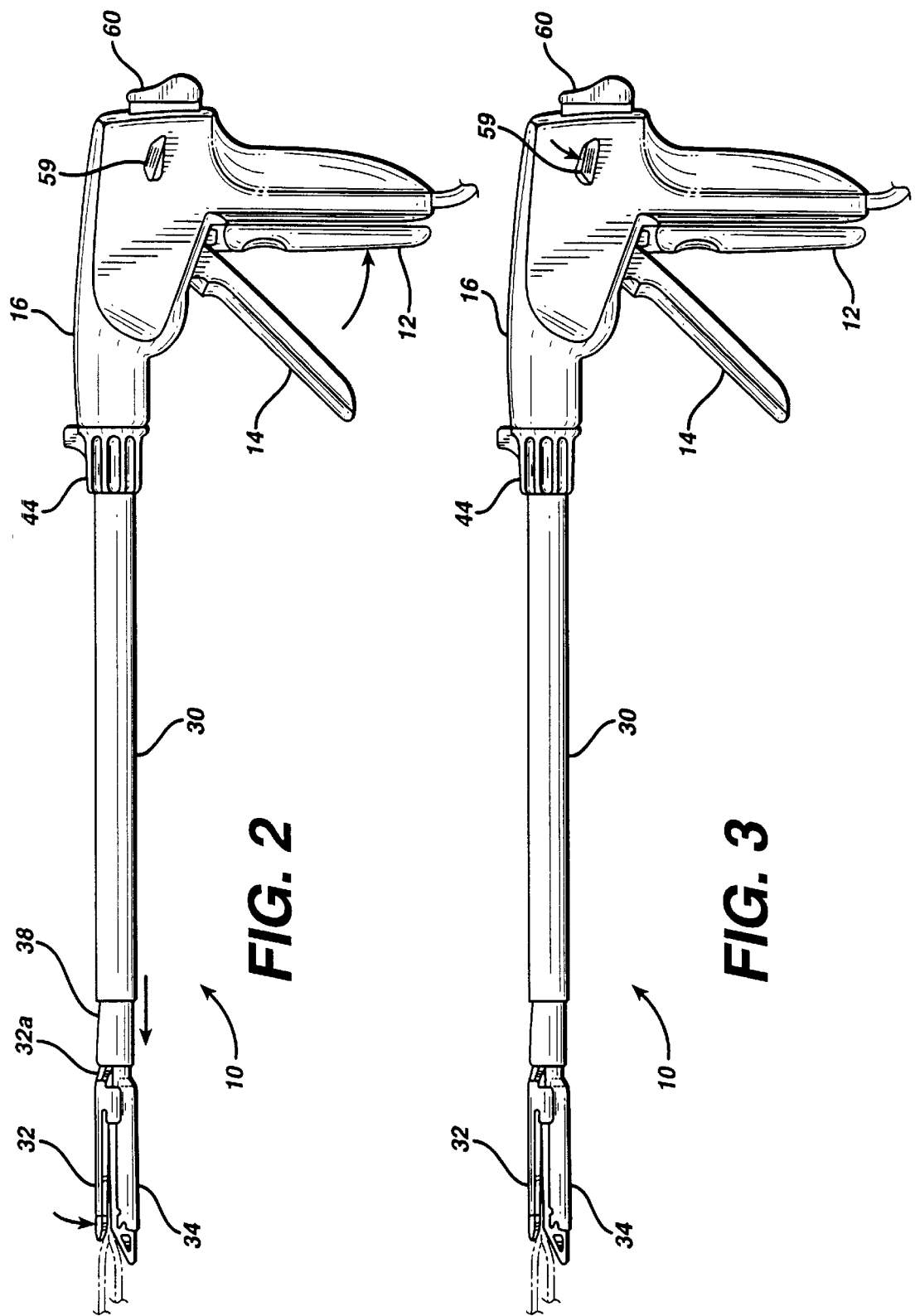

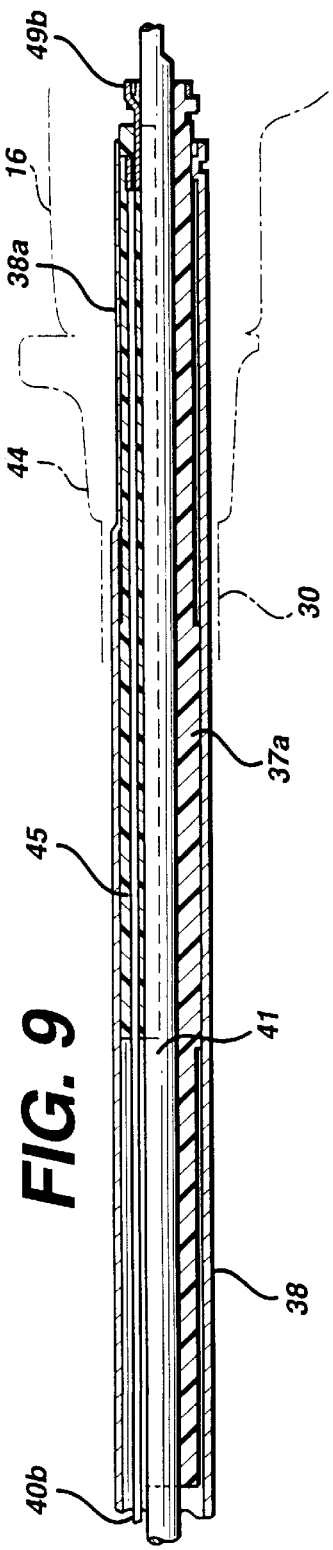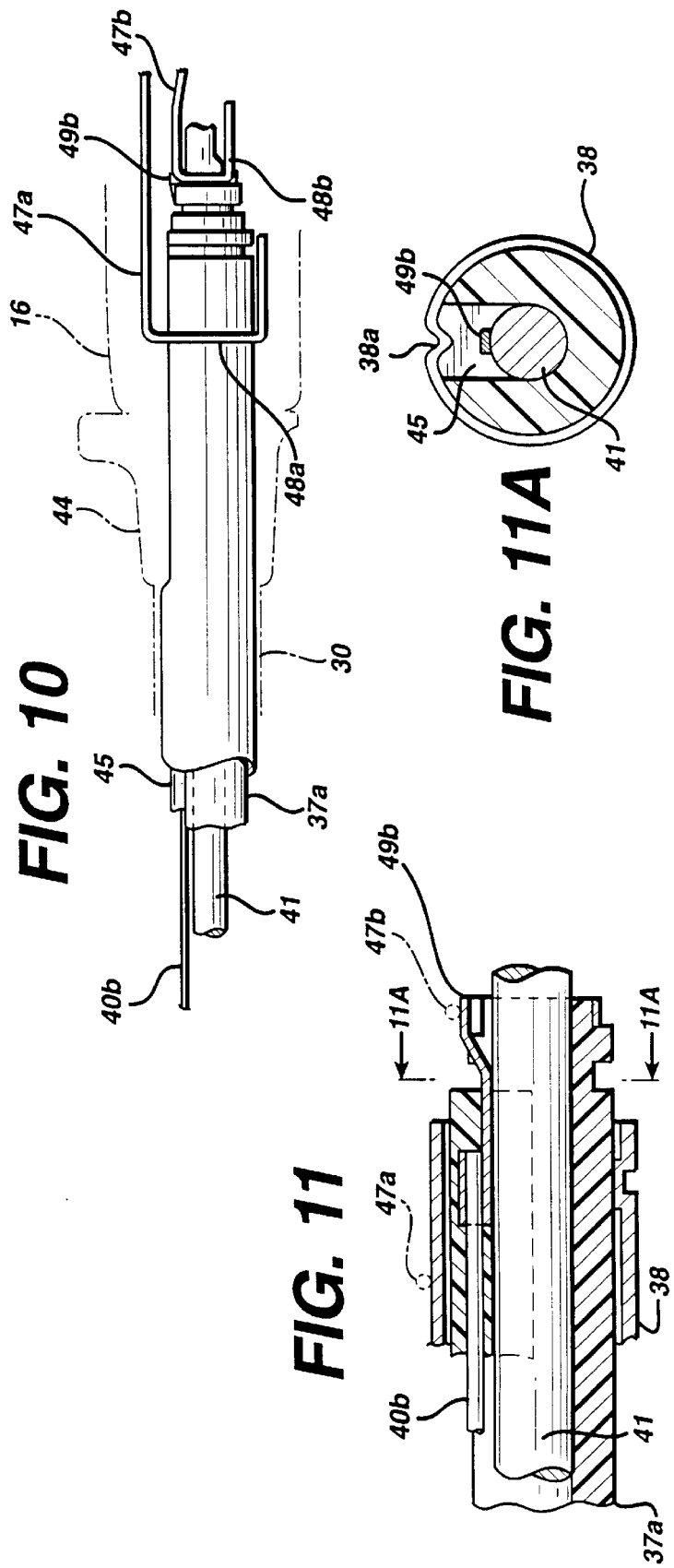

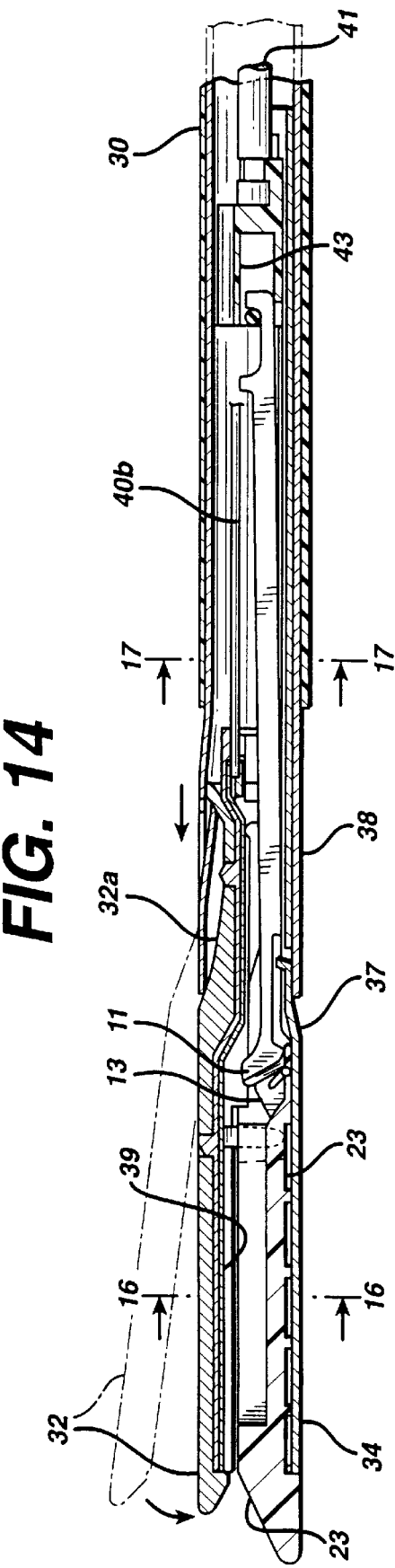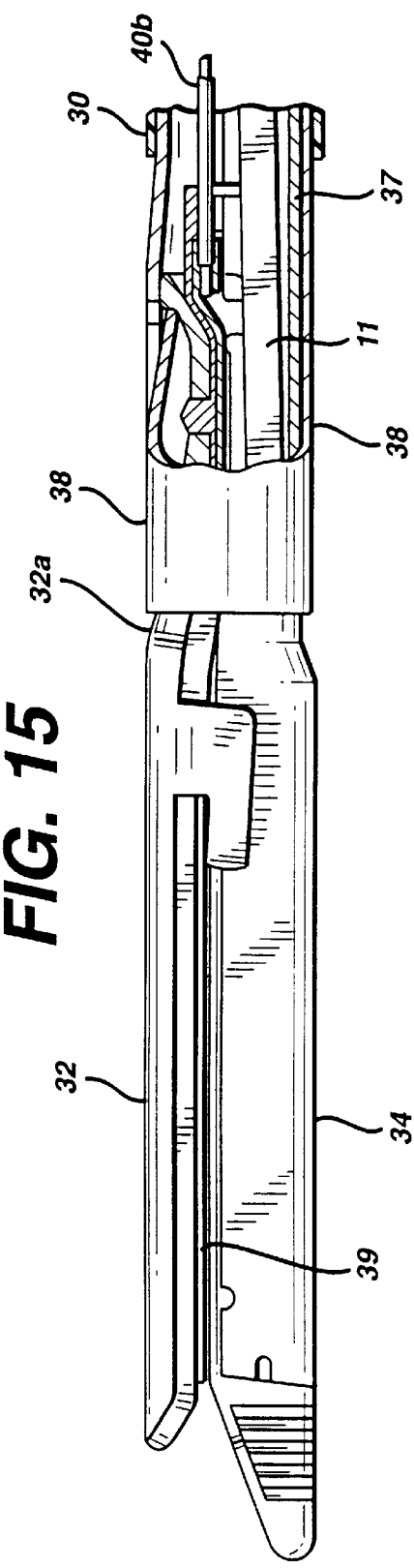

SURGICAL TISSUE TREATING DEVICE WITH LOCKING MECHANISM

This is a continuation-in-part to U.S. application Ser. No. 08/362,070 filed on Dec. 22, 1992, now abandoned, which is a continuation-in-part of U.S. application Ser. No. 08/311,297, filed on Sep. 23, 1994, now U.S. Pat. No. 5,558,671, which is a continuation-in-part of U.S. application Ser. No. 08/095,797, now Pat. No. 5,403,312, filed on Jun. 22, 1993 incorporated herein by reference.

FIELD OF THE INVENTION

This invention relates to a locking mechanism for an electrosurgical instrument for cauterization, coagulation and/or tissue welding in the performance of surgical procedures, especially endoscopic procedures.

BACKGROUND OF THE INVENTION

Surgical procedures requiring cutting of tissue can cause bleeding at the site of the cutting. Various techniques have been adapted to control bleeding with varying degrees of success such as, for example, suturing, applying clips to blood vessels, and stapling, as well as electrocautery and other tissue heating techniques. Advances in tissue joining or welding, tissue repair and wound closure also have permitted surgical procedures previously not possible or too risky.

Surgical staplers have been used for tissue security, joining, and approximation, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows. In these devices, lockout mechanisms have been described to prevent refiring of single-shot staple cartridges.

Electrosurgical devices have been used for effecting improved hemostasis by heating tissue and blood vessels to cause coagulation or cauterization. U.S. Pat. No. 5,403,312 discloses a clamping and cutting device that clamps tissue, applies electrosurgical energy to the tissue and cuts the tissue. A described preferred embodiment also applies staples to tissue held by the device. Other instruments have been used for cutting and coagulating tissue, using other tissue heating energies, such as, for example, ultrasound, laser, thermal and infrared light.

It is desirable to provide a means for controlling a hemostatic tissue heating device with cutting and/or stapling functions, to prevent an improper sequential application of these functions. For example, to prevent cutting before providing hemostasis. It is also desirable to provide a means for preventing instrument use when the staple cartridge is empty, before tissue heating energy has been applied, or when tissue treatment is incomplete.

SUMMARY OF THE INVENTION

Accordingly, it is an object of the present invention to provide a hemostatic tissue treating instrument with a locking mechanism to ensure proper sequence of operation of the device.

A preferred embodiment provides a surgical instrument with a tissue treating portion having a therapeutic energy delivering device arranged to deliver therapeutic energy to tissue and a tissue manipulation device. Therapeutic energy is energy, e.g., electrosurgical, heat, light, ultrasonic, etc., used to treat tissue to cause a therapeutic effect, e.g. to heat, cut, coagulate, weld, cauterize, etc., tissue. A tissue manipulation device is a device which is used to treat or handle tissue with a mechanical means or a means having a mechanical effect on tissue, e.g., to divide, cut, join, fasten, clip, staple, etc.

The tissue treating portion of the preferred embodiment is coupled to a shaft. The shaft includes a therapeutic energy communication device which provides therapeutic energy to the therapeutic energy delivering device in the tissue treating portion. Such energy communication device may comprise wires or conductors to supply electrical energy to an electrode or heater, a metal shaft to deliver ultrasonic energy, light fibers to deliver laser or light energy, etc.

A tissue manipulation actuating device actuates the tissue manipulating device and a locking mechanism moves or alters the manipulation actuating device from a locked to an unlocked position or visa versa. Preferably this occurs after delivery of therapeutic energy to tissue has been initiated or completed.

The preferred embodiment further includes a tissue parameter measurement and instrument control device which provides a feedback signal representative of tissue treatment status e.g. welding or coagulation complete and is coupled to and/or controls the tissue treating portion, either directly or indirectly, by controlling energy delivered to the energy delivering device, by actuating the tissue manipulation device, by enabling or disenabling any one of these features, or by causing the device to operate or be user operated in a sequential manner. Various alternative features of the invention are described below.

One aspect of the invention provides a cutting device with an energy delivery means for tissue welding, coagulation or cauterization, particularly along a cutting path. The present invention provides a locking mechanism to prevent cutting or actuation of the cutting element until therapeutic energy is applied or until after coagulation, cauterization or welding has occurred.

In a preferred embodiment, electrosurgical energy is used, although other devices are contemplated by this invention. Accordingly, the invention will be described in use with an electrosurgical instrument.

In various embodiments of the present invention, electrosurgical energy may be applied in conjunction with application of one or more tissue fasteners such as, for example, staples, clips, absorbable fasteners, etc., using an applier to apply the fastener, such as a driver to drive staples into tissue. When in use with a cutting and stapling instrument the locking mechanism preferably prevents staple firing until after electrosurgical energy has been applied and prevents refiring once staples have been fired. Accordingly, a locking mechanism of one embodiment prevents actuation of the cutting element and staple drivers without application of RF energy or without proper hemostasis and then prevents refiring of a spent staple cartridge.

These and other objects of the invention are described in a preferred embodiment in which an electrosurgical device includes an end effector with opposing interfacing surfaces for engaging tissue therebetween, and two electrically different electrodes, corresponding to electrically different potentials, at least one electrode located on one or both of the opposing surfaces. Preferably, the electrodes are offset from each other with respect to interfacing surfaces, i.e., they are offset from each other so that they are not diametrically opposed from each other on an interfacing surface or surfaces.

An electrosurgical instrument of a preferred embodiment compresses tissue in a compression zone between a first interfacing surface and a second interfacing surface and applies electrical energy through the compression zone. The first interfacing surface is comprised of: a first electrode corresponding to a first pole of a bipolar energy source and a second electrode corresponding to a second pole of a bipolar energy source. The second electrode is located on the same or opposite interfacing surface as the first electrode. In this particular embodiment of the invention, the compression zone is an area defined by a compression ridge on one or more of the interfacing surfaces, which compresses the tissue against the other interfacing surface. A coagulation zone is defined by the first electrode, the second electrode, and an insulator insulating the first electrode from the second electrode.

In one preferred embodiment, the hemostatic device is incorporated into a linear cutter similar to a linear cutting mechanical stapler. In this embodiment the hemostatic device comprises two elongated electrode bars and a slot for a cutting means to cut tissue engaged by the end effector of the device. Preferably the bars are laterally adjacent an insulator forming a ridge to compress tissue to be cauterized. Optionally, one or more rows of staples may be provided on each side of the slot and bars to provide mechanical tissue security or approximation during the healing process. In operation, tissue is clamped between two jaws. Electrical energy in the form of radio frequency current is applied to the compressed tissue to cauterize the tissue. The device provides hemostatic lines adjacent the path of the cutting element. Other cutting and stapling instruments may be used as well, such as, for example, an interluminal circular cutting instrument.

The lockout mechanism of the present invention may include mechanical, electrical and/or electro-mechanical locking elements and may be actuated in response to a control signal, from a controller.

In one embodiment, an indicator communicates to the user that the tissue has been cauterized to a desired or predetermined degree. In the preferred embodiment, a tissue impedance sensor is incorporated into the device to determine coagulation status based on measured tissue impedance. The impedance sensor may include a controller which provides a control signal based on the tissue treatment status. The control signal may be used to control the generator, to electrically control the locking mechanism and/or to provide a perceivable signal to a user.

These and other objects of the invention will be better understood from the following attached Detailed Description of the Drawings, when taken in conjunction with the Detailed Description of the invention.

DETAILED DESCRIPTION OF THE DRAWINGS

FIG. 2 is a side elevational view of the embodiment of FIG. 1 shown in a closed, clamped position, before cutting or stapling;

FIG. 3 is a side elevational view of the embodiment of FIG. 2 shown as RF energy is applied to tissue;

FIG. 9 is a longitudinal cross-sectional view of the intermediate portion of the instrument;

FIG. 10 is an elevational view of the proximal end of the intermediate portion showing the contact of the wireforms to their respective contact positions;

FIG. 11 is an enlarged cross-sectional view of the proximal end of the intermediate portion of the instrument;

FIG. 11a is a transverse cross sectional view taken along the lines 11a —11a of FIG. 11;

FIG. 14 is a longitudinal cross-sectional view of the distal end of the instrument of FIG. 1 shown in a closed and clamped position;

FIG. 15 is an enlarged partial cross-sectional view of the distal portion of FIG. 13;

DETAILED DESCRIPTION OF THE PREFERRED EMBODIMENTS

While the present invention is generally applicable to a variety of electrosurgical instruments including monopolar, bipolar and multipolar (i.e., including two or more therapeutic electrodes providing energy in waveforms as measured from any pole to any other pole as having a phasic relationship), and both conventional and endoscopic, it will be described herein with reference to an endoscopic bipolar linear cutting and stapling instrument.

Operation of linear cutting and stapling instruments are known in the art and are discussed, for example, in U.S. Pat. Nos. 4,608,981, and 4,633,874.

Figure 1:
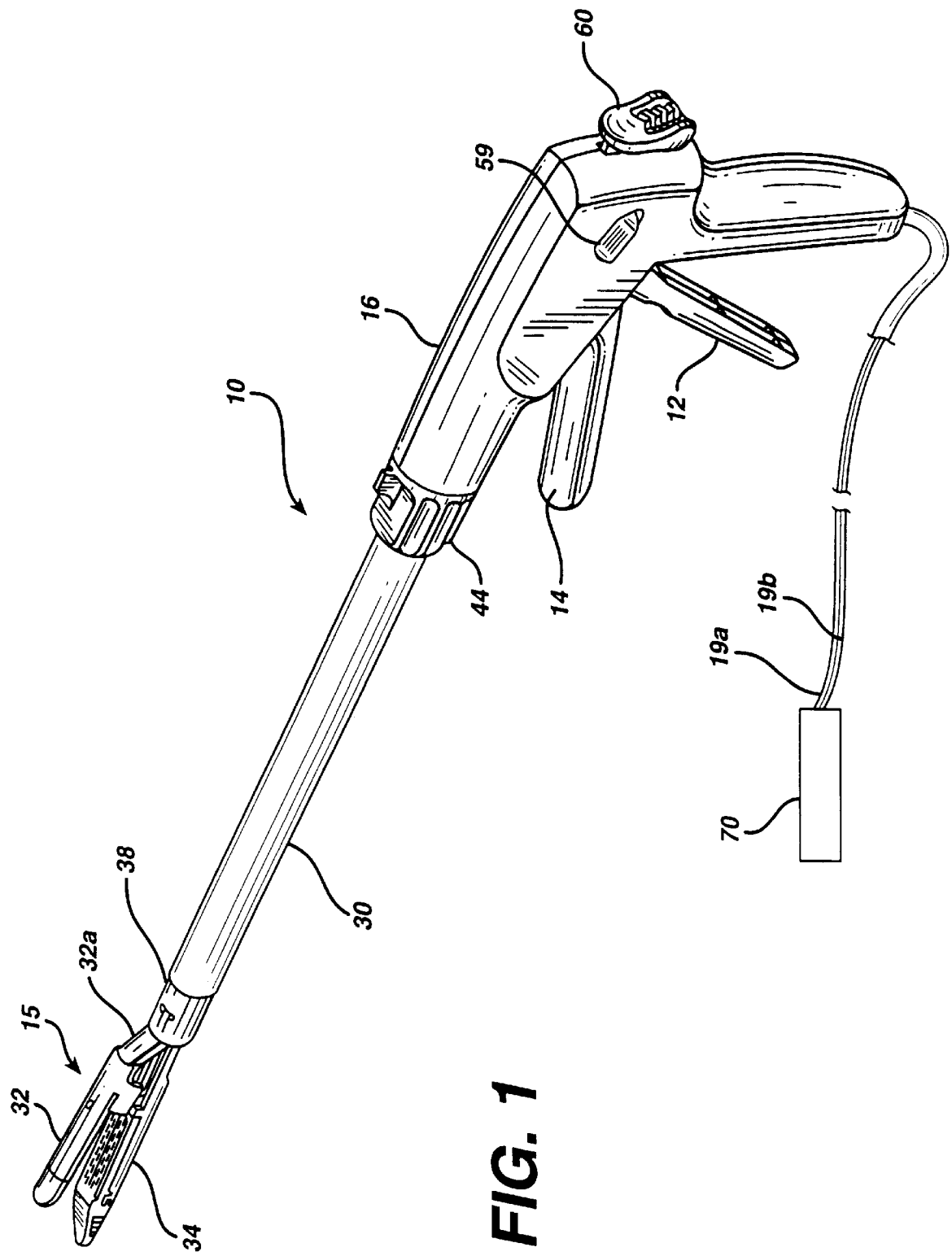
FIG. 1, is a perspective view of an endoscopic electrosurgical instrument of one embodiment of the present invention.
Figure 4:
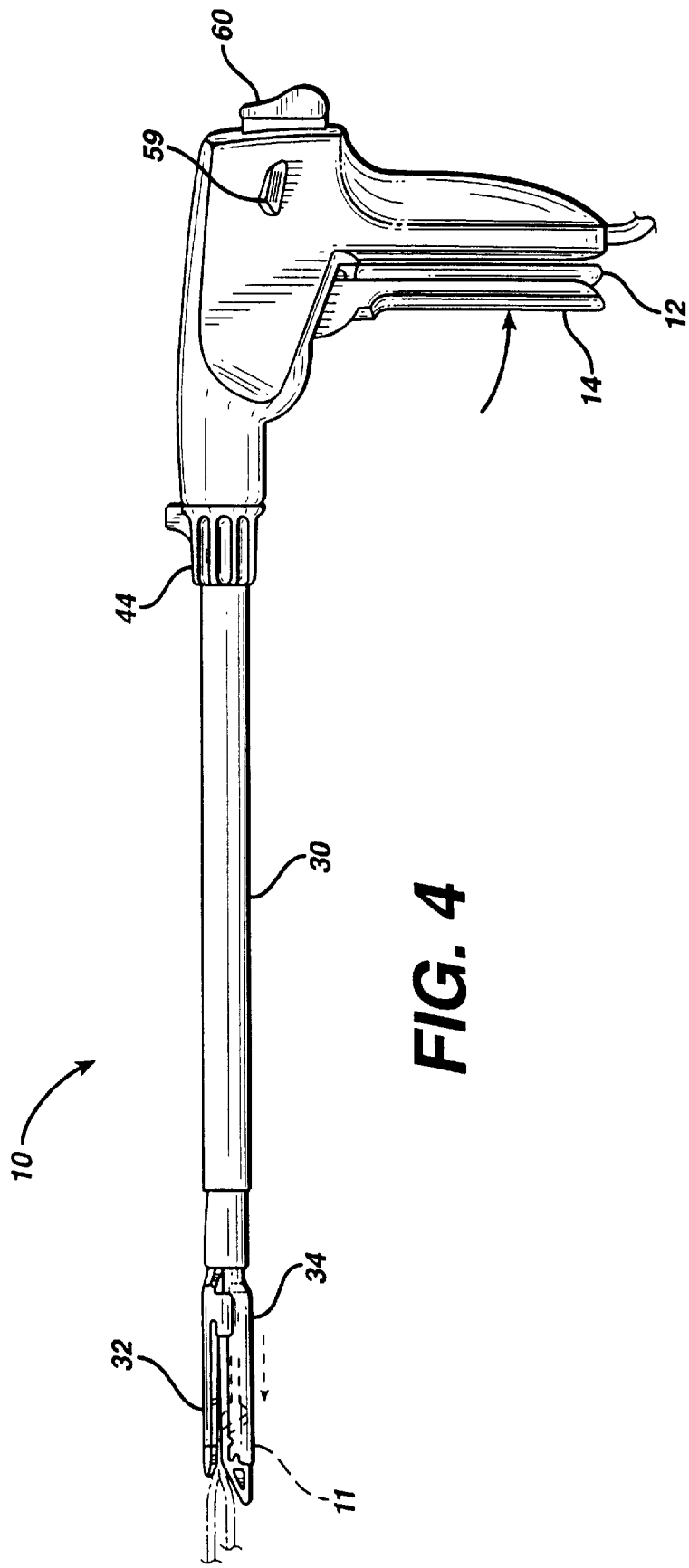
FIG. 4 is a side elevational view similar to FIG. 3 shown after RF energy has been applied and the tissue has been stapled and cut.
Figure 5:
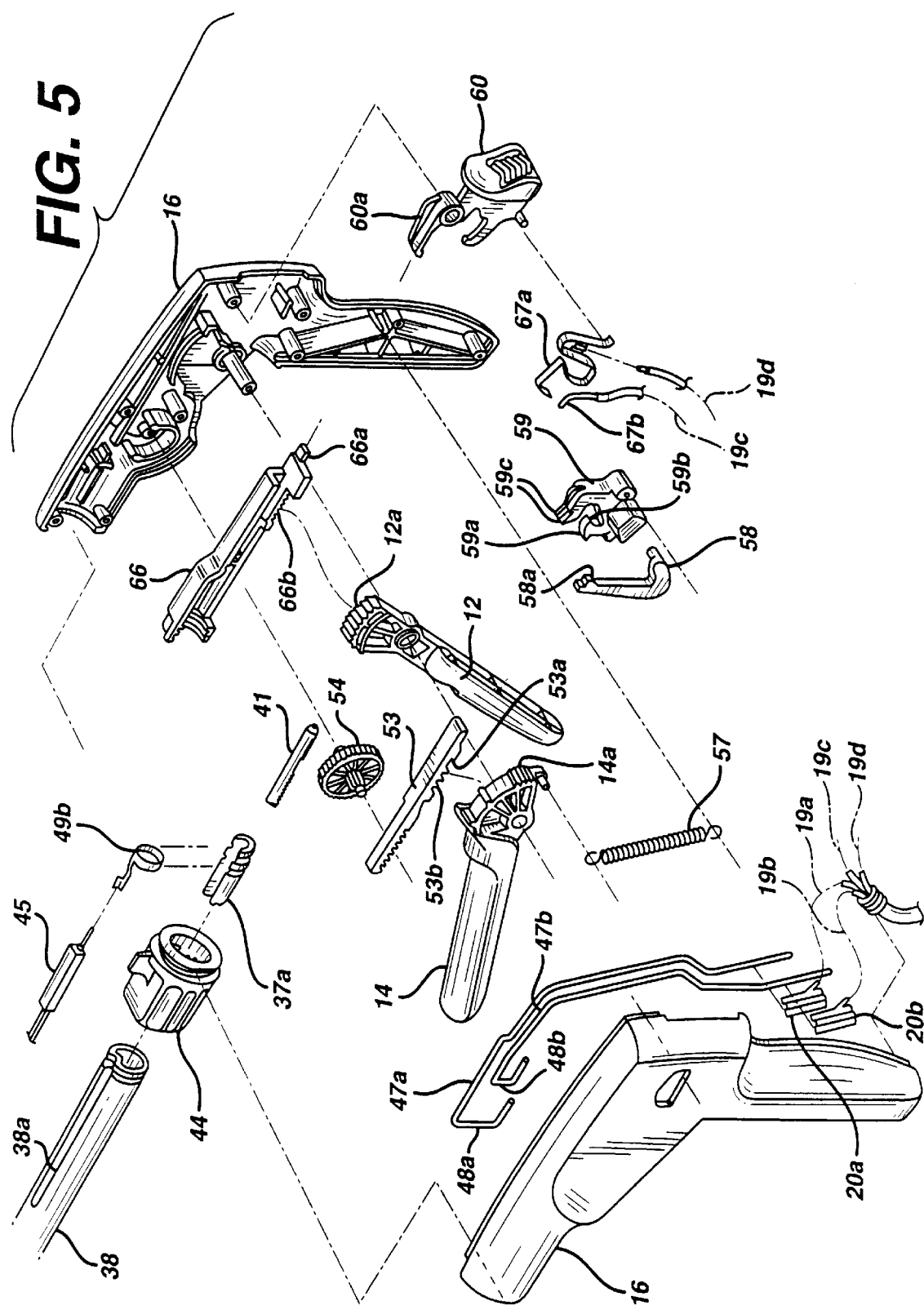
FIG. 5 is an exploded perspective view of the proximal handle portion of the instrument of FIG. 1.
Figure 6:
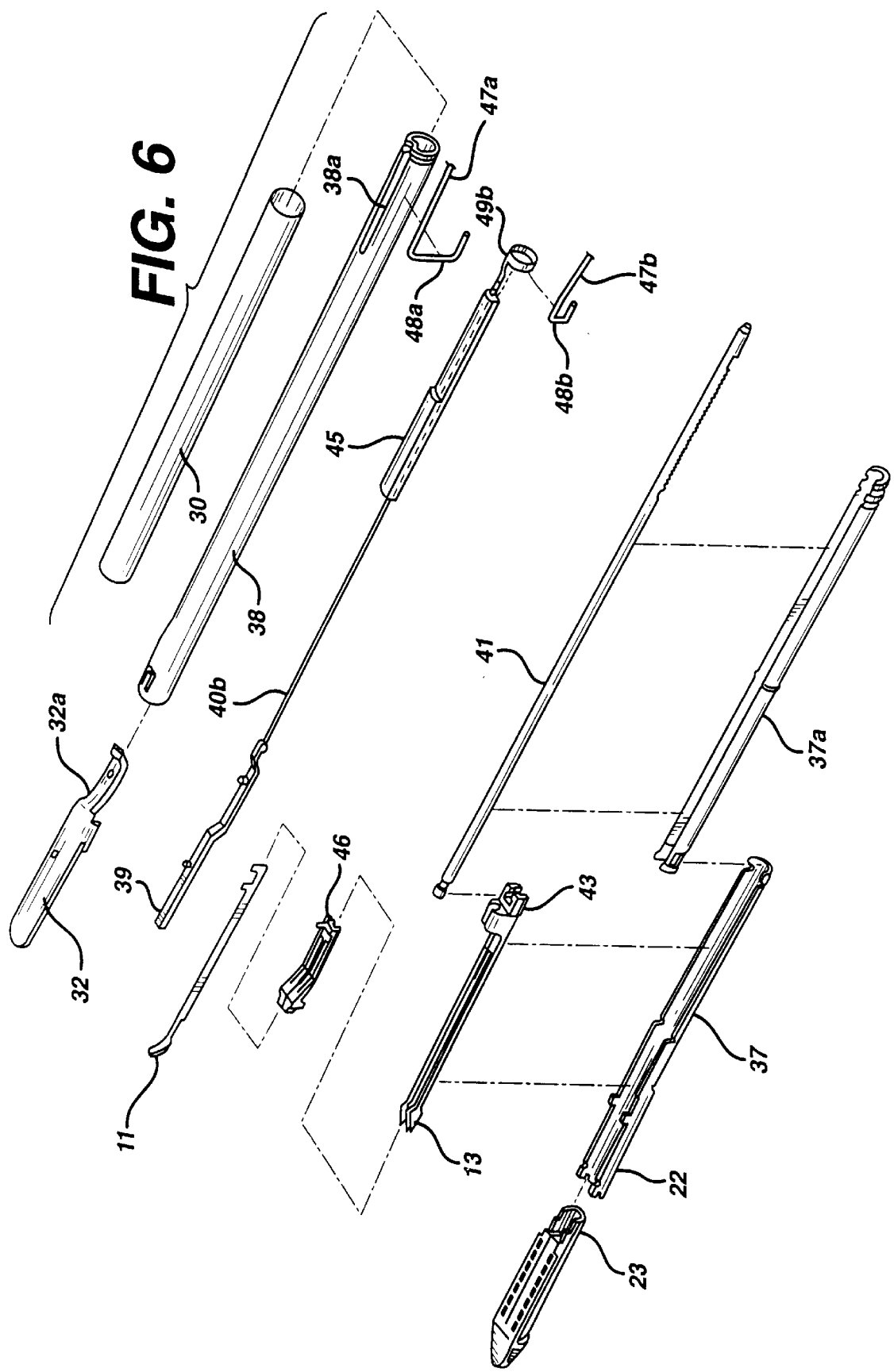
FIG. 6 is an exploded perspective view of the intermediate and distal portion of the instrument of FIG. 1.
Figure 7:
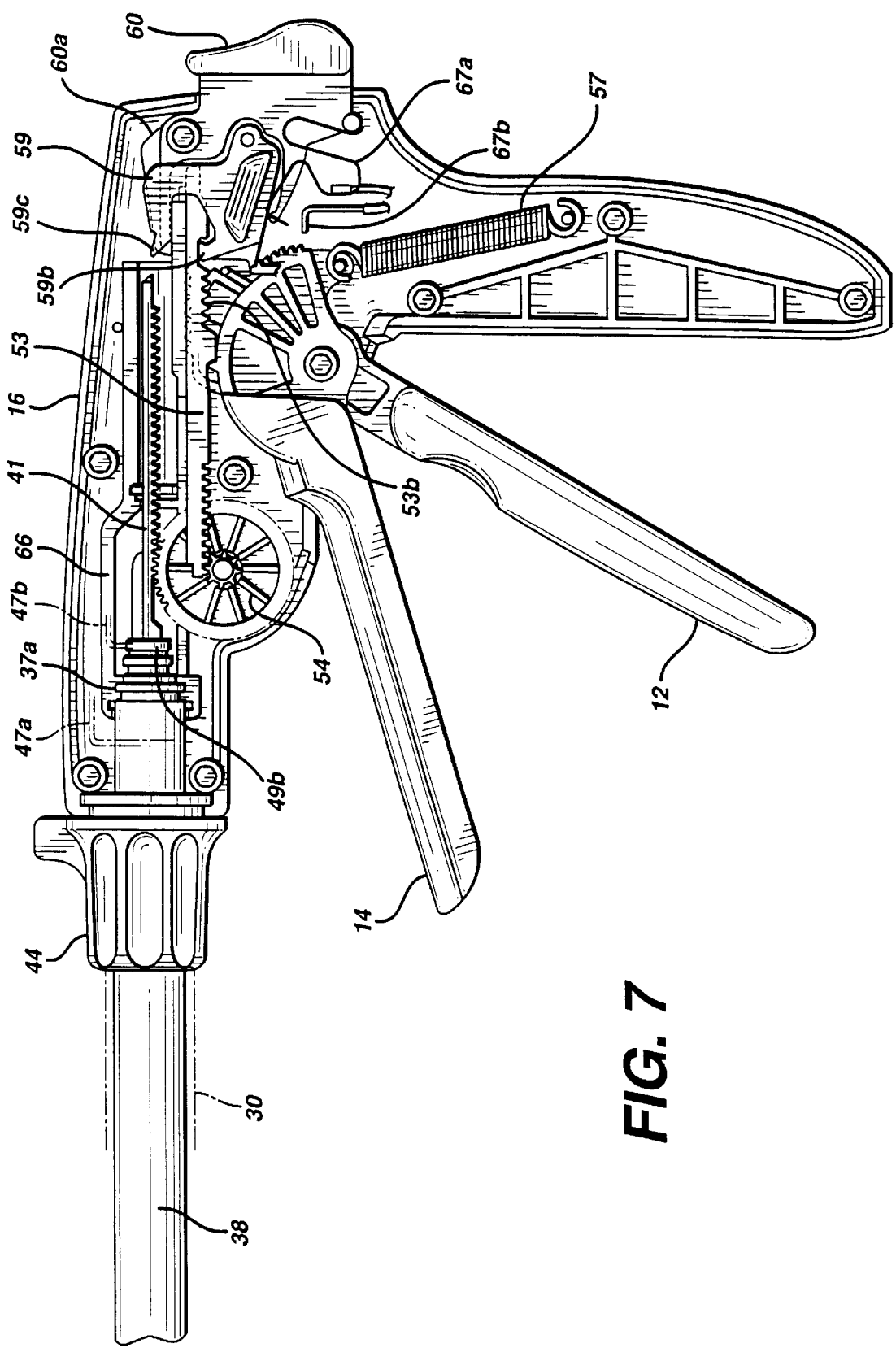
FIG. 7 is a side elevational view of the proximal handle portion in a first, open position of the instrument of FIG. 1, shown with the left side handle cover and wireforms removed.
Figure 8:
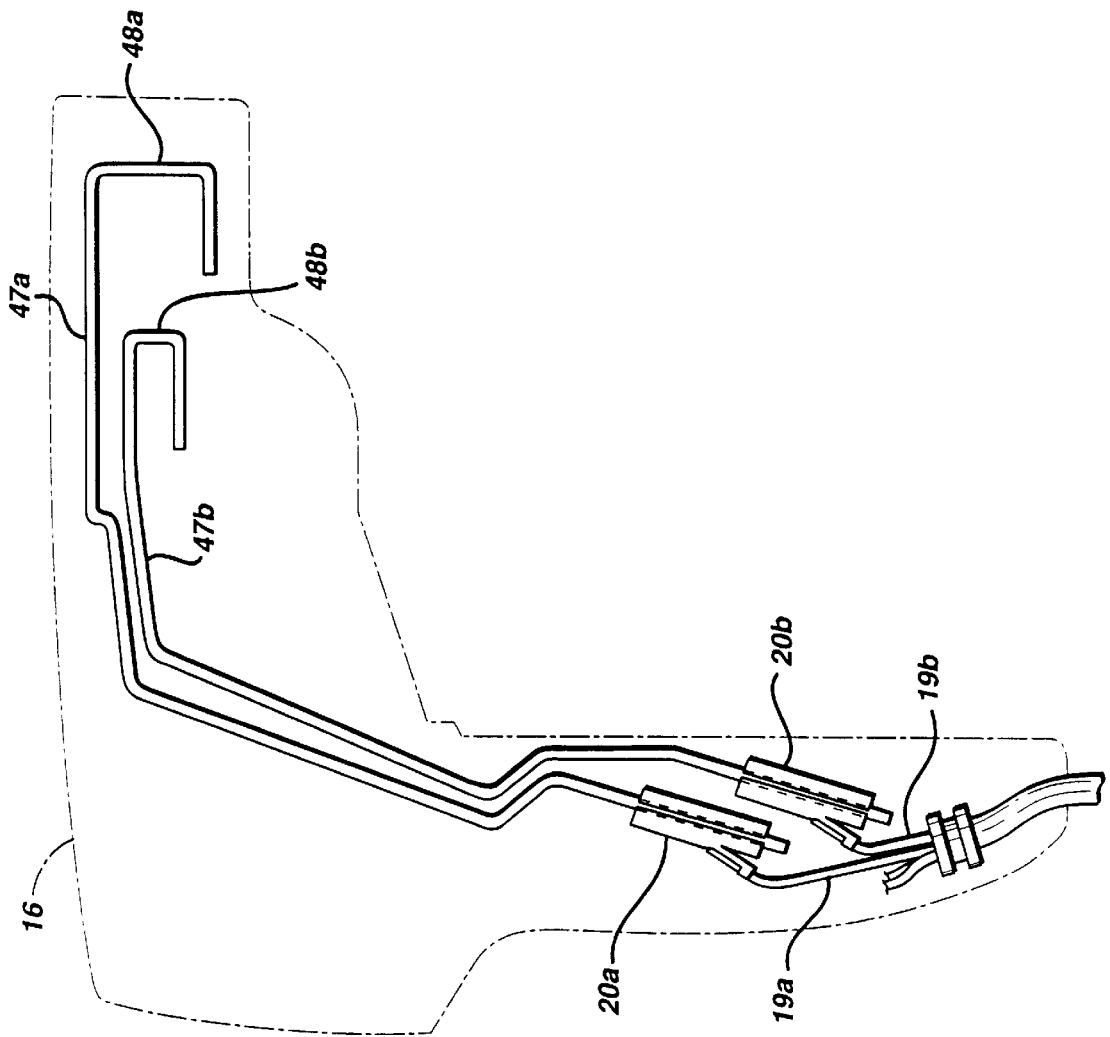
FIG. 8 is an elevational view of the inside of the left side handle portion showing the location of the wireforms and connectors used in the present invention.
Figure 13:
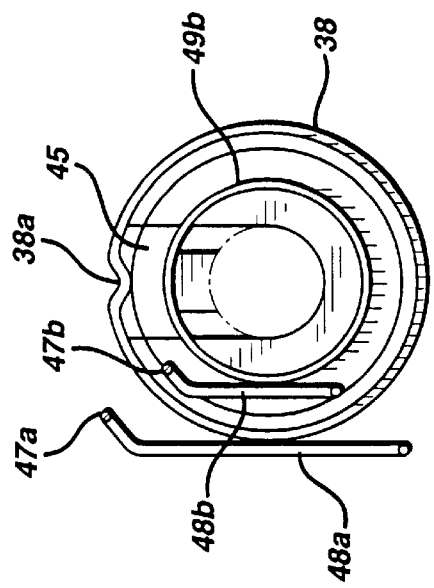
FIG. 13 is an end view of FIG. 11 showing a slight bias in the wireforms allowing for pressure of the wireforms onto their respective contact positions.
Figure 12:
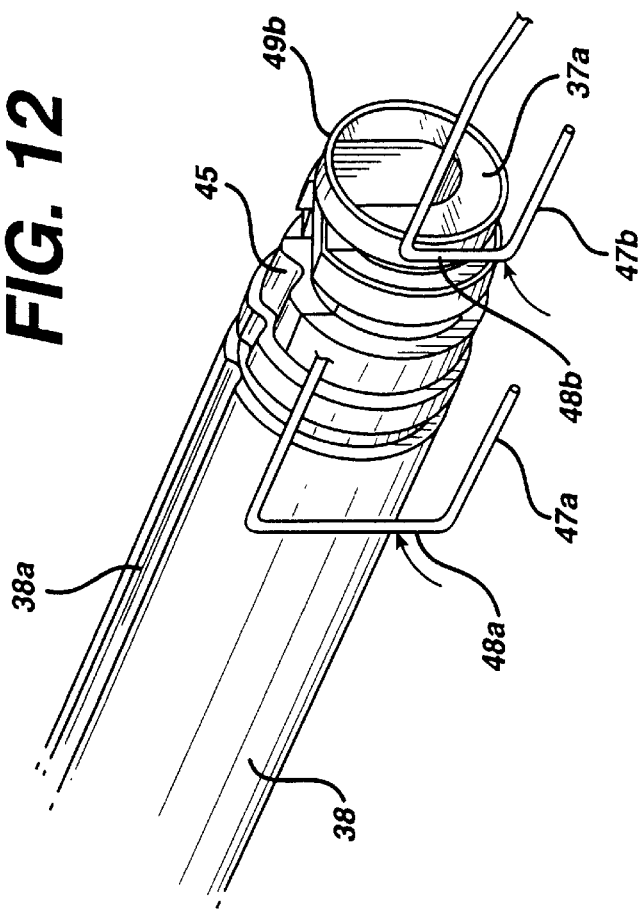
FIG. 12 is a perspective view showing the wireforms contacting their respective contact position.

Referring now to FIGS. 1–17 there is illustrated an instrument of the present invention to be used in conjunction with an impedance feedback device. An endoscopic linear cutting and stapling instrument 10 is shown having a housing 16 coupled to a sheath 30 with a lumen extending therethrough and an end effector 15 extending from the distal end of the sheath 30. The end effector 15 comprises first and second elements which are comprised of interfacing jaw members 32, 34. Jaw member 32 is movably secured to jaw member 34. The housing 16 has a clamping trigger 12 for closing jaw members 32, 34, an RF switch detente arm 58 and electrical switch contacts 67a, 67b, coupled to an electrical switch 59 for turning on RF energy, and a firing trigger 14 for advancing the cutting element 11 through tissue and wedge 13 for applying staples 17. Jaw members 32, 34 are shown in an unclamped position in FIG. 1; in a clamped position prior to application of electrosurgical energy and prior to cutting and stapling in FIG. 2; in a clamped position after application of electrosurgical energy and prior to cutting and stapling in FIG. 3; and in a clamped position after cutting and stapling in FIG. 4.

Figure 16:
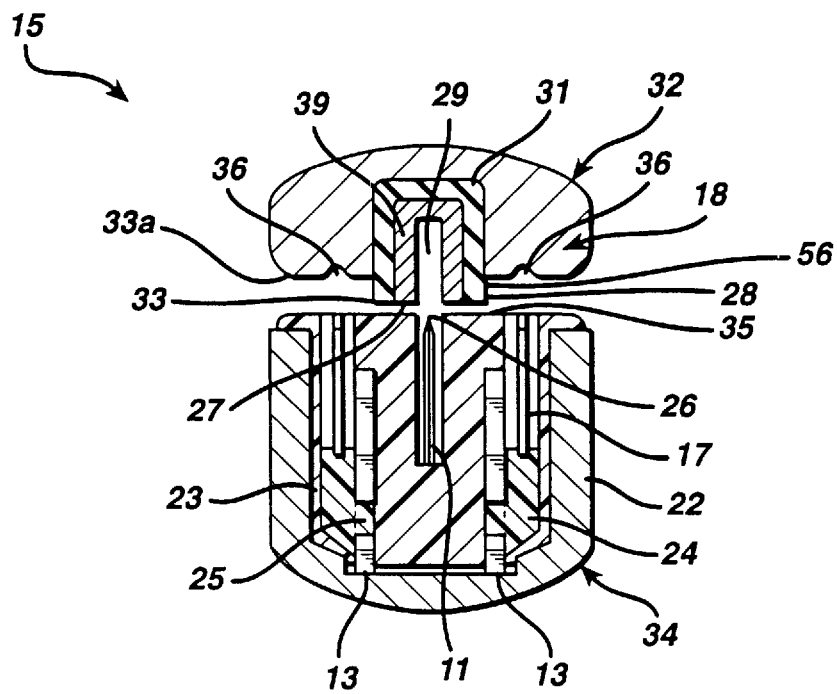
FIG. 16 is a transverse cross-sectional view taken along line 16—16 of FIG. 14.
Figure 17:
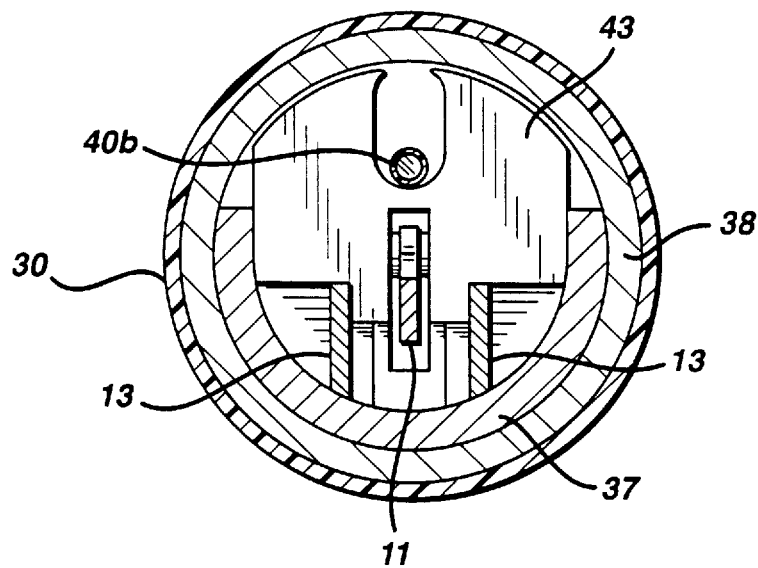
FIG. 17 is a transverse cross-sectional view taken along line 17—17 of FIG. 14.

Jaw member 32 comprises an anvil 18, U-shaped therapeutic electrode 39 extending along the length of the jaw 32, and a U-shaped insulating material 31 surrounding the outside of the therapeutic electrode 39. Jaw member 32 has an inner surface 33 which substantially faces an inner surface 35 of jaw member 34. The U-shaped electrode 39 comprises two electrically communicating electrode bars 27, 28 forming a first pole and located on and extending substantially along the length of the inner surface 33. The U-shaped electrode 39 is comprised of a conductor, such as, aluminum or surgical grade stainless steel. The U-shaped insulator is preferably formed of a polymer such as polyphenyleneoxide. The bars 27, 28 are separated by a knife channel 29 extending longitudinally through the middle of the electrode 39. Pockets 36 located on anvil 18 for receiving staple ends are located along the inner surface 33, along the length and outside of bars 27, 28, to form a row of staples on each side of electrode 39. The electrode bars 27, 28 and insulating material 31 form a ridge 56 extending out relative to an anvil portion 33a of the inner surface 33 (FIG. 16). The electrode 39 acts as a first pole of a bipolar tissue treatment or therapeutic system. The anvil 18 is formed of an electrically conductive material and acts as a second therapeutic electrode of the bipolar treatment or therapeutic system, the anvil being electrically opposite of the treatment electrode 39. The anvil 18 is electrically isolated from electrode 39 by the U-shaped insulating material 31.

Jaw member 34 comprises a cartridge channel 22 and a cartridge 23 releasably inserted into the cartridge channel 22. The cartridge 23 includes a track 25 for wedge 13, a knife channel 26 extending longitudinally through the center of the cartridge 23, a series of drivers 24 extending into the track 25 and staples 17 arranged in two sets of single rows.

The sheath 30 is formed of an insulative material and has an electrically conductive closure tube 38 extending through its lumen. In a preferred embodiment, the closure tube 38 acts as a jaw closure tube and as an electrical contact. A channel retainer 37a extends from the proximal end of the closure tube 38 and is secured to channel 37 which there extends distally through the remainder of the closure tube 38 to form jaw member 34. The channel 37 includes cartridge channel 22 extending distally from the closure tube 38.

The body 16 has a clamping trigger 12 for advancing the closure tube 38 to close the jaws 32, 34 towards each other engaging tissue therebetween. Rotation of the clamping trigger 12 causes the closure tube 38 to advance co-axially through the sheath 30 over a camming surface 32a of jaw 32 to close the jaws 32, 34 onto tissue situated between the jaws 32, 34.

The channel retainer 37a guides co-axial movement of a drive rod 41 within the channel 37. The drive rod 41 is advanced by the rotation of the firing trigger 14 as described in more detail below. The driving rod 41 is coupled on its distal end to a block 43. The block 43 is coupled to a cutting means 11 and a staple driving wedge 13, which the drive rod 41 advances by way of the block 43 into the end effector 15. A wedge guide 46 is used to guide wedge 13 into track 25. Jaw member 32 is secured by way of the channel 37 to the jaw member 34.

When the drive rod 41 advances the cutting element 11, the cutting element 11 advances through the knife channel 26 in between the bars 27, 28 to cut tissue engaged by jaws 32, 34 when the tissue has been cauterized. Thus, the cut line is medial to the coagulation lines formed by the bar electrodes 27, 28. The drive rod 41 simultaneously advances the block 43 and thus the wedge 13 which drives the drivers 24 into the staples 17 causing the staples 17 to fire through tissue and into the pockets 36 of the anvil 18. Staples 17 are applied in single longitudinal rows on each side of the cutting element 11 as the cutting element 11 cuts the tissue.

A knob 44 located on the distal end of the body 16 rotates the closure tube 38, channel retainer 37a, channel 37 and end effector 15 which are directly or indirectly coupled to the knob 44 so that the knob 44 may be used for rotational placement of the end effector jaws 32, 34. The knob 44 includes a peg (not shown) which fits into and engages indentation 38a closure tube 38. Closure tube 38 is fitted at its proximal end, into the housing 16.

Electrical energy is supplied to the electrode 39 and anvil 18, 70 through connections such as those described below, or other connections means, such as, for example, like those described in U.S. Pat. No. 5,403,312, incorporated herein by reference. The generator 70 is user controlled by way of RF switch 59 located in the housing 16. Wires 19c, 19d extend from switch 59 to a controller included with the generator 70 as described below.

Wires 19a and 19b extend into the body 16 of the instrument and deliver energy to electrodes 39, 18 respectively. Wires 19a, 19b are coupled to low impedance contact elements 20a, 20b respectively and contact elements 20a, 20b are coupled to wireforms 47a, 47b respectively. Wireforms 47a, 47b are exposed at their distal ends 48a, 48b. Wireforms 47a and 47b are biased respectively towards closure tube 38 and contact ring 49b located on the proximal end of channel retainer 37a, so as to make electrical contact with the closure tube 38 and ring 49b respectively.

Wire 19a delivers electrical current to the anvil 18 by way of first wire form 47a which contacts electrically conductive closure tube 38 which contacts electrically conductive anvil 18 as closure tube 38 closes jaws 32, 34.

Wire 19b delivers electrical current to the electrode 39 through second wire form 47b which contacts contact ring 49b coupled to wire 40b extending through the closure tube 38 to the electrode 39.

The closure tube 38 and ring contact 49b permit the knob 44 to rotate while contact is maintained between closure tube 38, ring 49b, and wireforms 47a, 47b, respectively. The ring 49b is electrically insulated from the closure tube 38.

Wire 40b extends through seal 45 which fits into channel retainer 37a, which fits into closure tube 38.

Clamping trigger 12 includes gear teeth 12a which movably engage with teeth 66b of yoke 66. Yoke 66 is coupled on its distal end to the closure tube 38. When clamping trigger 12 is actuated, the gear teeth 12a engage with teeth 66b in yoke 66 causing the yoke 66 to advance distally.

Closure tube 38 closes jaws 32, 34 as it advances over camming surface 32a of jaw 32.

The RF switch 59 is rotated to switch on RF energy to be supplied to the therapeutic electrodes. When the RF switch 59 is rotated, detente protrusion 59a on the switch 59 hooks under detente protrusion 58a on detente arm 58, preventing the switch 59 from deactivating RF energy unless the RF switch 59 is manually rotated back to its original position. The RF energy may also be turned off electrically.

Switch 59 has a moveable contact 67a and a stationary contact 67b. The moveable contact 67a rotates with switch 59 to contact stationary contact 67b when switch is on. A signal is supplied to the generator 70 through wires 19c, 19d coupled to stationary contact 67b and moveable contact 67a respectively.

Ledge 60a of release button 60 is engaged with the proximal end of the yoke 66 adjacent step ledge 66a on proximal end of yoke 66. When the yoke 66 is advanced by the clamping trigger 12, the ledge 60a rotates down behind proximal end of yoke 66, thereby preventing yoke 66 from retracting until release button 60 has been pressed. Thus the jaws 32, 34 will remain in a closed position until a user releases the jaws 32, 34 with release button 60.

The switch 59 includes fingers 59c which sit just above proximal end of yoke 66. The ledge 60a of the release button 60 fits in between fingers 59c. The RF switch 59 cannot be activated, i.e., rotated forward, until the yoke 66 has been advanced distally so that fingers 59c of switch 59 are free to rotate behind proximal end of yoke 66.

The switch 59 also includes a lower hook 59b which engages groove 53a of firing rack 53. Firing rack 53 includes gear teeth 53b which are engaged by gear teeth 14a of firing trigger 14. The firing rack 53 is coupled on its distal end to pinion gear 54 which in turn engages the drive rod 41.

When the firing trigger 14 is pulled, the fire rack 53 is advanced distally to rotate pinion 54 which advances the driving rod 41 distally to actuate the cutting element 11 and to drive staples 17 into tissue engaged by the end effector 15.

The firing rack 53 cannot advance however until the lower hook 59b of the RF switch is disengaged from the groove 53a of the firing rack 53. This occurs only when the RF switch 59 has been activated.

Thus, the presently described device includes a lockout device or devices for preventing application of RF energy, staples or knife actuation until the jaws 32, 34 have been closed. The lockout device(s) require the proper sequence is followed as illustrated in FIGS. 1–4 and 18, and as described in more detail below.

The present invention also provides a detented RF switch so that RF energy is continuously applied until the switch 59 is manually released or until the RF energy is switched off, e.g., by an electrical feedback control signal to the generator 70.

The closure trigger 12 and firing trigger 14 are interlocked and a spring 57 is mechanically coupled to both triggers 12, 14.

When tissue is engaged between clamped jaw members 32, 34, and RF energy has been applied, the firing trigger 14 located on housing 16 may be actuated to advance a cutting element 11 through the engaged tissue to cut the tissue. Simultaneously, when the firing trigger 14 is actuated, the wedge 13 is advanced through the track 25 causing the drivers to 24 to displace towards the staples 17, thereby driving the staples 17 through tissue and into anvil pockets 36.

A preferred embodiment of the present invention includes a feedback system designed to indicate when a desired or predetermined tissue effect has occurred. An audible, visible, tactile, or other feedback system may be used to indicate when sufficient cauterization has occurred at which point the RF energy may be turned off. In a particular embodiment, the feedback system measure one or more electrical parameters of the system, e.g., the electrical impedance of the tissue to which the electrical energy is applied, to determine tissue characteristics, e.g., coagulation complete. An example of such a feedback system is described in U.S application Ser. No. 08/311,297, filed on Sep. 23, 1994, incorporated herein by reference.

Using such a feedback system, an electrical signal may be provided to turn off RF energy. Such a signal may be used to electrically open a locking mechanism to permit a cutting element actuation or application of staples. After the RF energy is turned off, the cutting means 11 is advanced and the staples 17 are fired using the firing trigger 14.

In one embodiment, the cartridge provides multifire stapling capabilities by having single rows of staples, as opposed to the convention double row of staples of the cartridges in the laparoscopic stapling and cutting devices presently in use. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. The device of the present may however, if desired, include double, triple, etc., staple rows. Also, in a further embodiment, no staples are required and the electrical coagulation lines provide the necessary hemostasis or tissue welding effect. A cartridge is defined herein to mean a staple containing mechanism.

Figure 18:
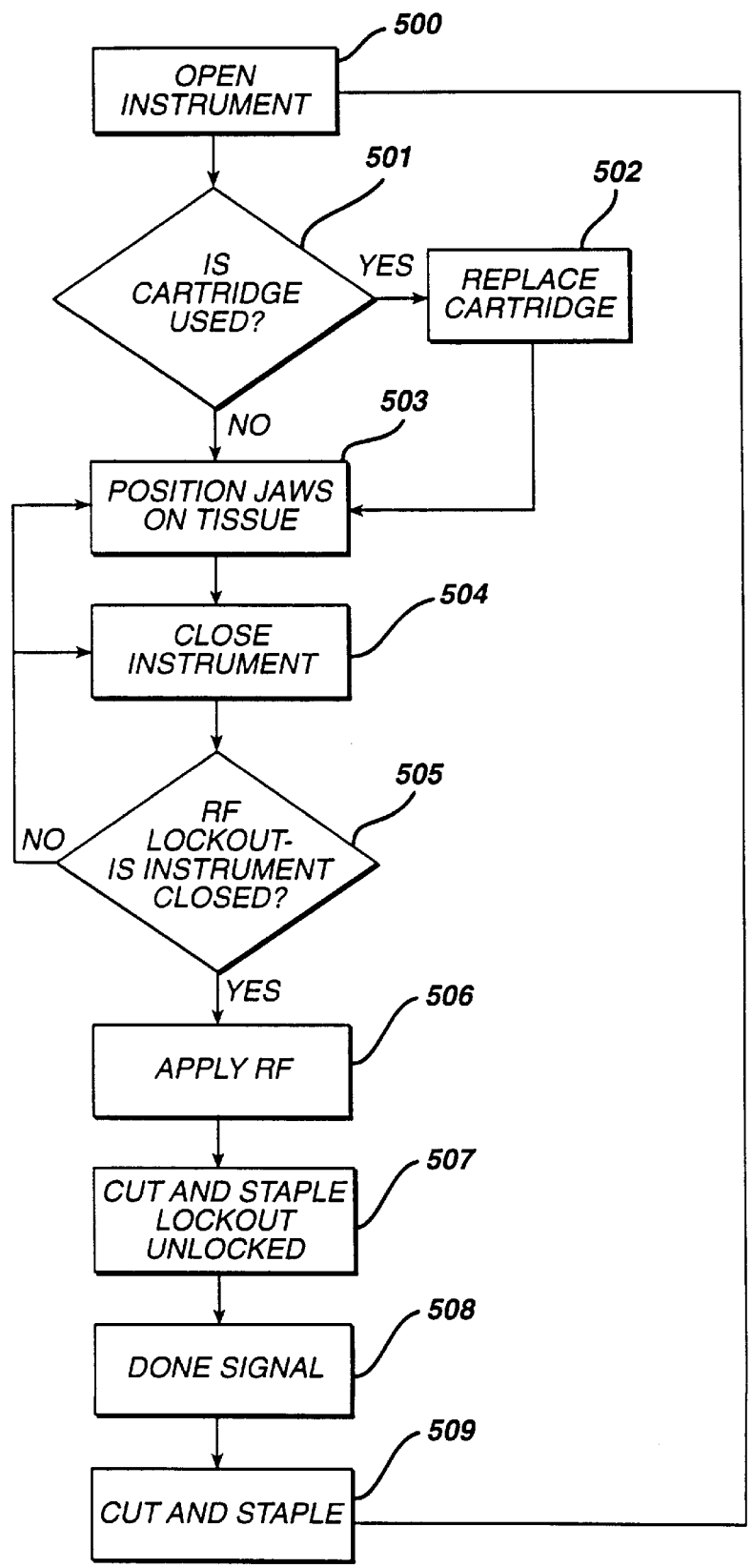
FIG. 18 is a flow chart illustrating the use of the instrument of FIG. 1 with a locking mechanism of the present invention.

Referring to FIG. 18, a preferred method of operation of the instrument of FIGS. 1–17 is illustrated. The jaws 32, 34 of the instrument 10 are opened by pressing button 60 (block 500). If the cartridge 22 has been used, the cartridge is replaced (blocks 501, 502). Then, the jaws 32, 34 are positioned on tissue (block 503) The instrument 10 is then closed by actuating trigger 12 (block 504). If the instrument is not fully closed, the RF lockout remains in place and RF cannot be applied (block 505). The instrument must be a repositioned on tissue again and/or the instrument must be closed. If the instrument is fully closed, the RF switch may be activated by actuating RF switch 59 (block 506). Actuation of the RF switch 59 releases the cutting and stapling lockout (block 507). As RF energy is applied, tissue is treated and monitored for completion of tissue treatment. A done signal indicates to a user that treatment is complete and the generator output RF energy is controlled by a corresponding generator control signal (block 508). The user may then actuate cutting and stapling with trigger 14 (block 509).

Figure 19:
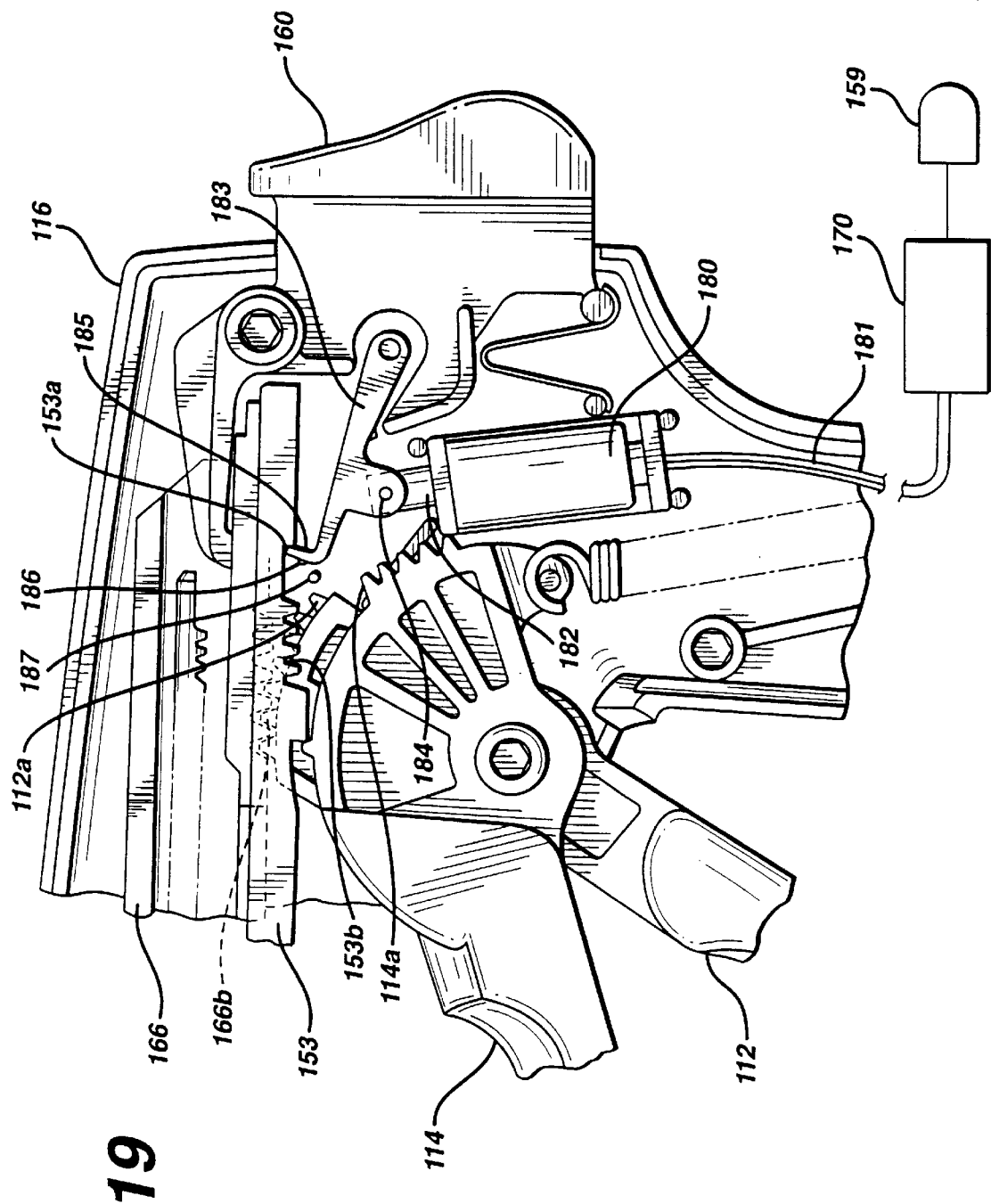
FIG. 19 illustrates a side view of a handle member of an alternative embodiment of a locking mechanism in a locked position.
Figure 20:
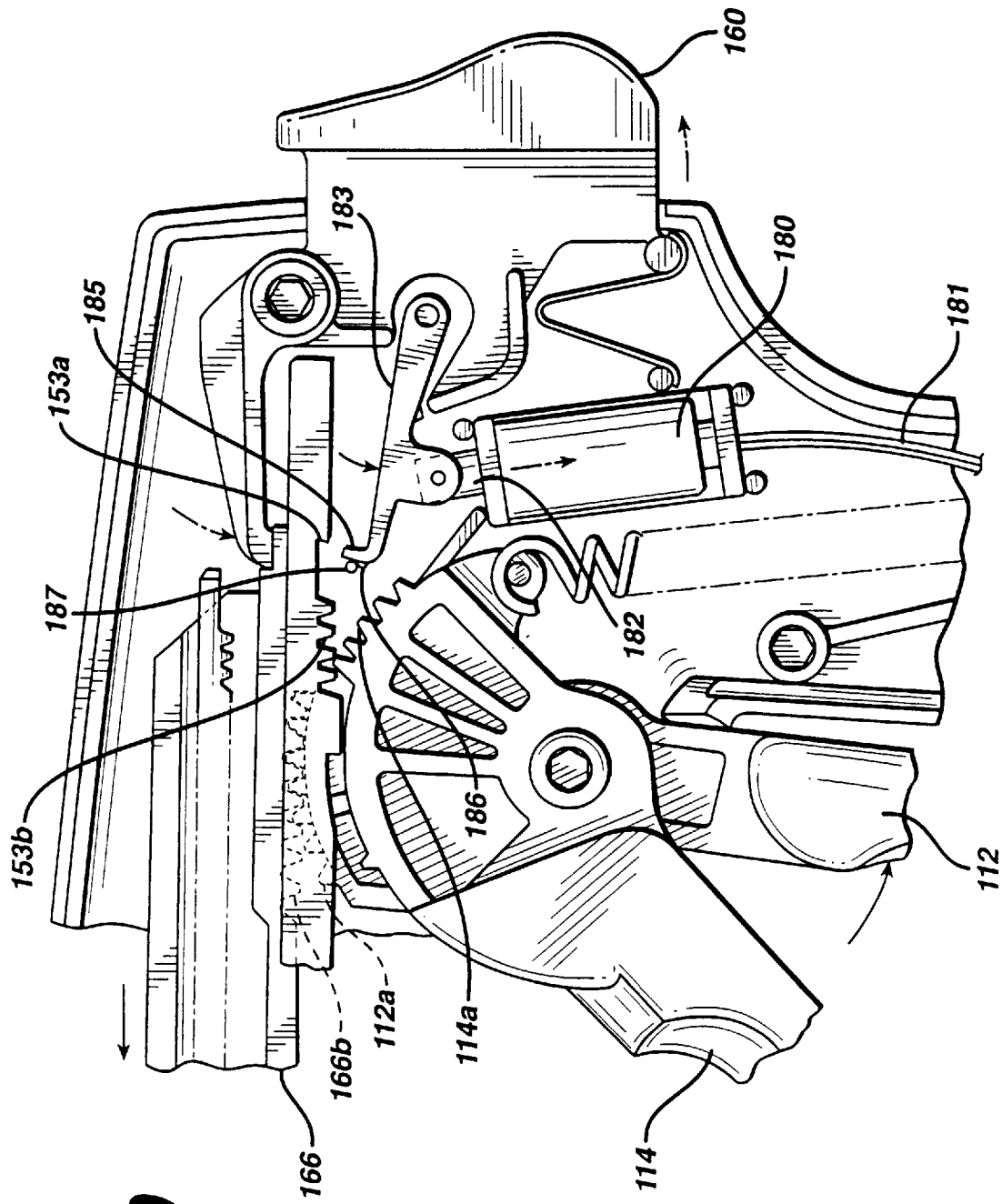
FIG. 20 illustrates a side view of the handle of the instrument in FIG. 19 with the locking mechanism in an unlocked position.
Figure 21:
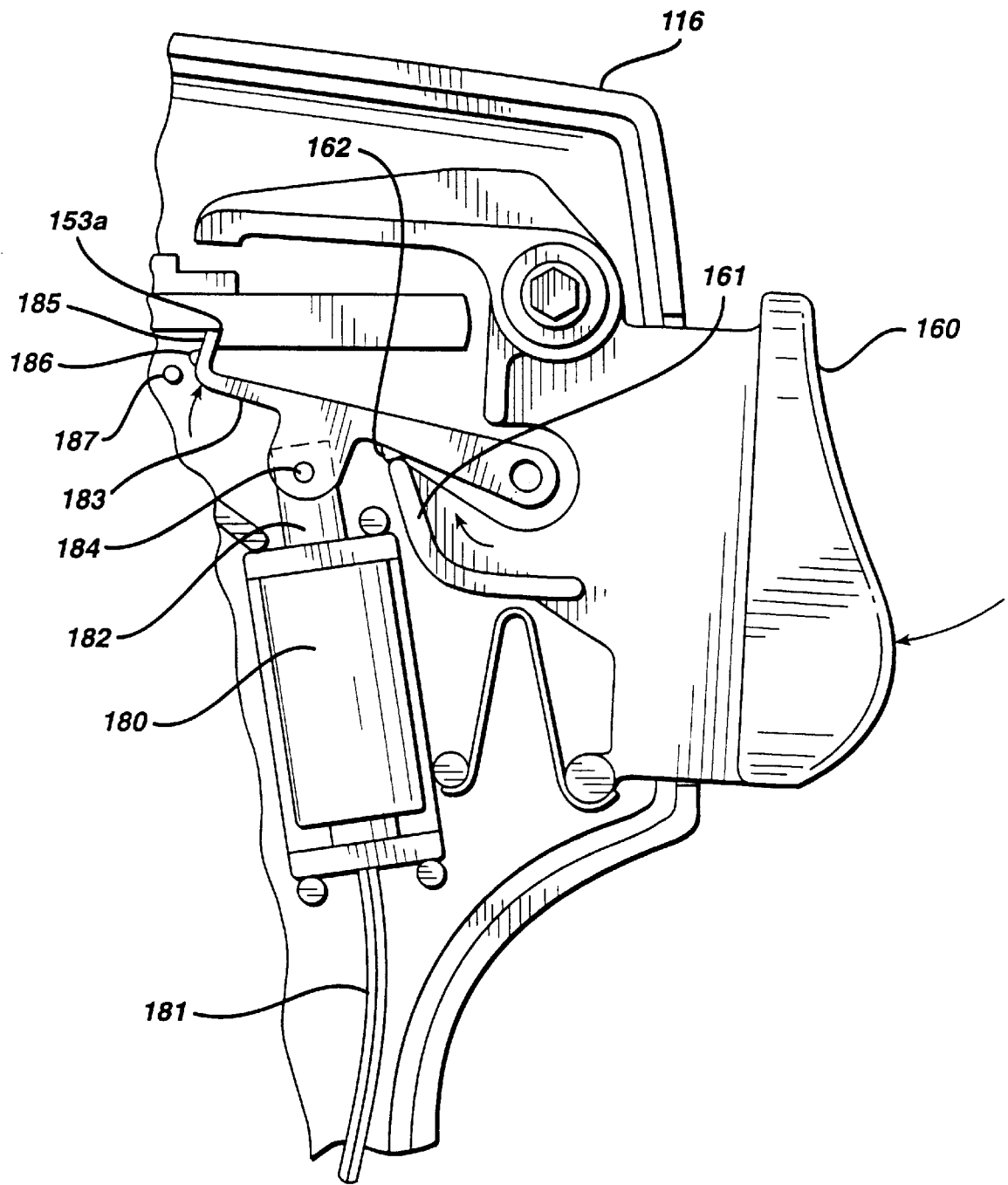
FIG. 21 illustrates a side view of the handle of FIGS. 19 and 20 as showing the locking mechanism being reset after firing.

Referring now to FIGS. 19–21, there is illustrated an alternative embodiment of the lockout of the present invention. A handle or housing 116 is illustrated having a clamping trigger 112 and a firing trigger 114. The clamping trigger 112 is arranged to advance the closure tube (not shown) similar to that illustrated in FIGS. 1–17, by engaging teeth 166b of yoke 166 with gear teeth 112a of clamping trigger. As the yoke 166 is advanced distally, the closure tube closes jaws of the end effector in a similar manner as that illustrated with respect to FIGS. 1–17.

An RF switch 159 is activated by a user to provide RF energy to the end effector (not shown) of the instrument. (The end effector of the instrument of this embodiment is configured in the same manner as that in FIGS. 1–17.) The RF switch may be located, for example, on the handle 116 or as a foot switch. The RF switch 159 signals to the generator to supply energy to the end effector.

The instrument may alternatively include an RF switch which acts in a manner just as that described in FIGS. 1–17 in which an RF switch on the handle cannot be activated until the jaws have closed, i.e., the yoke has been advanced distally.

The generator is arranged to receive impedance information of the tissue being treated by the end effector. Such a device and method are illustrated in U.S. application Ser. No. 08/311,297, filed on Sep. 23, 1994. When the generator has detected a coagulation complete condition using the tissue impedance feedback, a signal is provided to an electro-mechanical lockout mechanism as described below.

The electro-mechanical lockout mechanism comprises a solenoid 180 which receives an electrical signal through wires 181 from the generator 170. The solenoid 180 is a pull solenoid which includes a movable end 182 which moves downwardly in response to an appropriate signal delivered through wires 181. The end 182 of the solenoid 180 is coupled to a mechanical lever 183 through pin 184. The lever 183 includes a hook 185 with a detent knob 186. In a locked position, the hook 185 engages with a groove 153a of a firing rack 153. The firing rack 153 includes gear teeth 153b which are engaged by gear teeth 114a of firing trigger 114. The firing rack 153 acts to advance the cutting element and staple drivers in the end effector in a manner similar as that described in FIGS. 1–17.

Once the jaws have been closed using the clamping trigger 112 and the RF energy has been turned on using the footswitch 159, a signal must be sent to the solenoid 180 through wires 181 to cause the solenoid 180 to pull the lever 183 so that hook 185 is rotated away from the groove 153a of the firing rack 153 thereby freeing the firing rack 153 to advance distally. A tissue monitor incorporated with the generator 170 determines if the coagulation has been completed using an impedance feedback monitor. Upon completion of coagulation, a control signal is sent from wires 181 to the solenoid 180 to cause the end 182 to retract into the solenoid 180. This causes the lever 183 to rotate the hook 185 away from the rack 153. The detent 186 on the lever 183 engages with detent 187 located in the housing to hold the lever 183 away from the rack 153.

After the staples are fired, the release button 160 must be pressed to release the jaws from their closed position and thus the instrument from the tissue. The release button 160 includes a finger 161 which engages with the ledge 162 in the lever 183 when the release button 160 is pressed. The finger 162 causes an upward force on the ledge 162 which causes the lever 183 to release from detent 187 and reengage the groove 153a of the firing rack 153 with the hook 185 of the lever 183.

Figure 22:
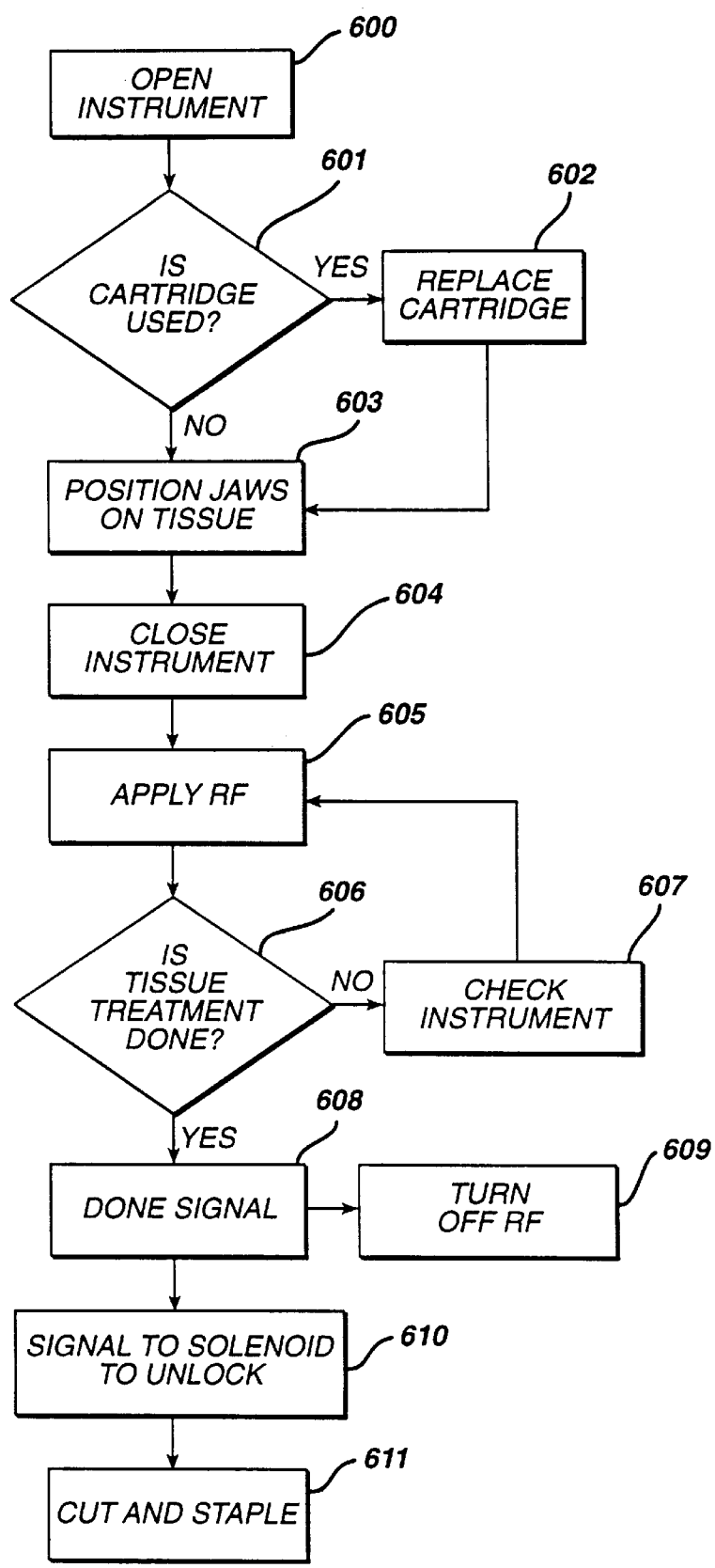
FIG. 22 is a block diagram illustrating a preferred use of the lockout devices of FIGS. 19–21.

Referring now to FIG. 22, a method of using the instrument of FIGS. 19–21 is illustrated. The jaws of the instrument 110 are opened by pressing release button 160 (block 600). If the cartridge has been used, the cartridge is replaced (blocks 601, 602). Then, the jaws of the instrument are positioned on tissue (block 603) and are closed by trigger 112 (block 604). RF energy is applied by the user by activating the footswitch 159 once the user has determined that the jaws are appropriately positioned on tissue (block 605). The tissue is monitored for completion of treatment (blocks 606, 607) using a tissue monitor feedback device such as, for example, the device described in U.S. application Ser. No. 08/311,297. A tissue treatment done signal is provided when treatment is completed. When tissue treatment is complete, RF energy is turned off (block 609) and the solenoid 180 is activated to release the cutting and stapling lockout (block 610). The cutting and stapling mechanisms may then be actuated (block 610).

Several variations of this invention have been described in connection with specific embodiments involving electrosurgical hemostatic devices and endoscopic cutting and stapling. Naturally, the invention may be used in numerous applications where hemostasis in desired. Also, the locking mechanism may be used in numerous devices where a tissue treating energy is used and prior to cutting and/or stapling by the instrument. Various hemostatic energies may be used prior to cutting, stapling or other mechanical manipulation of tissue, such as, ultrasonic energy, thermal energy, laser energy, infrared light energy, etc. Various tissue monitoring parameters or means may be used to provide a responsive electro-mechanical feedback signal. For example, electrical impedance, mechanical impedance, temperature or light absorption or reflectance may be used as feedback to generate the feedback signal. Accordingly, it will be understood by those skilled in the art that various changes and modifications may be made in the invention without departing from its scope, which is defined by the following claims and their equivalents.

What is claimed is:

1. A surgical instrument comprising:
    a tissue treating portion including: a therapeutic energy delivering device arranged to deliver therapeutic energy to tissue, and a tissue manipulation device;
    a shaft coupled to said tissue treating portion, said shaft including a therapeutic energy communication device operatively coupled to said therapeutic energy delivering device said energy delivering device and said energy communication device adapted to be actuated to deliver therapeutic energy to tissue;
    a tissue manipulation actuating device having a locked position and an unlocked position, said tissue manipulation actuating device extending through said shaft and operatively coupled to said tissue manipulation device;
    a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue;
    a tissue parameter measurement and instrument control device adapted to provide a feedback signal representative of a tissue treatment status of tissue being treated by said therapeutic energy delivering device, said parameter measurement and instrument control device coupled to said tissue treating portion of said instrument; and
    a status indicator coupled to said parameter measurement and instrument control device, said status indicator arranged to provide a user perceptible signal indicating a tissue treatment status.

2. The surgical instrument of claim 1 wherein the tissue treatment status is coagulation complete.

3. A surgical instrument comprising:
    a tissue treating portion including: a therapeutic energy delivering device arranged to deliver therapeutic energy to tissue, and a tissue manipulation device;

a shaft coupled to said tissue treating portion, said shaft including a therapeutic energy communication device operatively coupled to said therapeutic energy delivering device, said energy delivering device and said energy communication device adapted to be actuated to deliver therapeutic energy to tissue;

a tissue manipulation actuating device having a locked position and an unlocked position, said tissue manipulation actuating device extending through said shaft and operatively coupled to said tissue manipulation device; and a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue wherein said locking mechanism comprises an electro-mechanical device operatively coupled to said parameter measurement and instrument control device and arranged to receive the feedback signal, said locking mechanism being responsive to said feedback signal to move said tissue manipulation actuating device from said locked position to said unlocked position when said feedback signal indicates an appropriate tissue status; and a tissue parameter measurement and instrument control device adapted to provide a feedback signal representative of a tissue treatment status of tissue being treated by said therapeutic energy delivering device, said parameter measurement and instrument control device coupled to said tissue treating portion of said instrument.

4. The surgical instrument of claim 3 wherein said tissue status is completion of coagulation to a desired degree.

5. A surgical instrument comprising:

a tissue treating portion including: a therapeutic energy delivering device arranged to deliver therapeutic energy to tissue, and a tissue manipulation device;

a shaft coupled to said tissue treating portion, said shaft including a therapeutic energy communication device operatively coupled to said therapeutic energy delivering device said energy delivering device and said energy communication device adapted to be actuated to deliver therapeutic energy to tissue;

a tissue manipulation actuating device comprising a tissue cutting device and a tissue fastener applying device and having a locked position and an unlocked position, said tissue manipulation actuating device extending through said shaft and operatively coupled to said tissue manipulation device; and a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue.

6. A surgical instrument comprising:

a tissue treating portion including: a therapeutic energy delivering device arranged to deliver therapeutic energy to tissue, and a tissue manipulation device;

a shaft coupled to said tissue treating portion, said shaft including a therapeutic energy communication device operatively coupled to said therapeutic energy delivering device said energy delivering device and said energy communication device adapted to be actuated to deliver therapeutic energy to tissue;

a tissue manipulation actuating device having a locked position and an unlocked position, said tissue manipulation actuating device extending through said shaft and operatively coupled to said tissue manipulation device, wherein said tissue manipulation device comprises a tissue cutting device and a tissue fastener applying device, and wherein said tissue fastener applying device is a tissue stapling device;

a locking mechanism coupled to said tissue manipulation actuation device for moving said tissue manipulation actuating device from said locked position to said unlocked position after said therapeutic energy delivering device and said therapeutic energy communication device are actuated to deliver therapeutic energy to tissue.

7. An electrosurgical instrument comprising:

a shaft having a distal end;

an end effector located at the distal end of the shaft, said end effector adapted to receive electrosurgical energy therein, said end effector comprising:

first and second elements comprising first and second opposed tissue contacting surfaces respectively, said surfaces moveable relative to each other from an open, spaced-apart position for positioning tissue therebetween, to a closed position for engaging the tissue, at least a portion of one of said surfaces being electrically conductive and arranged to receive the electrosurgical energy;

a cutting element moveable to cut tissue engaged by said end effector;

an actuating device operatively coupled to the cutting element, said actuating device extending through said shaft to said cutting element and arranged to actuate said cutting element to cut tissue; and a locking mechanism operatively coupled to said actuating device, said locking mechanism having a first position in which said locking mechanism engages said actuating device to prevent actuation of said cutting element, and a second position in which said locking mechanism releases said actuating device to permit actuation of said cutting element.

8. The electrosurgical instrument of claim 7 wherein said locking mechanism comprises an electromechanical device.

9. The electrosurgical instrument of claim 7 further comprising a tissue parameter measurement and instrument control device adapted to provide a feedback signal representative of a tissue treatment status of tissue being treated by said at least one electrode, said parameter measurement and instrument control device coupled to said end effector of said instrument.

10. The electrosurgical instrument of claim 9 further comprising a status indicator coupled to said parameter measurement and instrument control device, said status indicator arranged to provide a user perceptible signal indicating a tissue treatment status.

11. The surgical instrument of claim 10 wherein the tissue treatment status is coagulation complete.

12. The surgical instrument of claim 9 wherein said locking mechanism comprises an electro-mechanical device operatively coupled to said parameter measurement and instrument control device and arranged to receive the feedback signal, said locking mechanism being responsive to said feedback signal to move said locking mechanism from said first position to said second position when said feedback signal indicates an appropriate tissue status.

13. A method for surgically treating tissue comprising:
providing a surgical instrument comprising:
- a tissue treating portion including: a therapeutic energy delivering device arranged to deliver therapeutic energy to tissue, and a tissue manipulation device;
- a shaft coupled to said tissue treating portion, said shaft including a therapeutic energy communication device operatively coupled to said therapeutic energy delivering device said energy delivering device and said energy communication device adapted to be actuated to deliver therapeutic energy to tissue;
- a tissue manipulation actuating device having a locked position and an unlocked position, said tissue manipulation actuating device extending through said shaft and operatively coupled to said tissue manipulation device; and
- a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue;

engaging tissue with said tissue treating portion;
applying therapeutic energy to treat said tissue;
determining that tissue treatment is complete;
then moving said locking mechanism from said locked position to said unlocked position; and
manipulating said tissue with said tissue manipulating device.

14. A method for surgically treating tissue comprising:
providing a surgical instrument comprising:
- a tissue treating portion including: a therapeutic energy delivering device arranged to deliver therapeutic energy to tissue, and a tissue manipulation device;
- a shaft coupled to said tissue treating portion, said shaft including a therapeutic energy communication device operatively coupled to said therapeutic energy delivering device said energy delivering device and said energy communication device adapted to be actuated to deliver therapeutic energy to tissue;
- a tissue manipulation actuating device having a locked position and an unlocked position, said tissue manipulation actuating device extending through said shaft and operatively coupled to said tissue manipulation device; and
- a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue;

engaging tissue with said tissue treating portion;
applying therapeutic energy to treat said tissue and moving said locking mechanism from said locked position to said unlocked position;
determining that tissue treatment is complete; and
manipulating said tissue with said tissue manipulating device.

15. A method for electrosurgically treating tissue comprising:
providing an electrosurgical instrument comprising:
- a shaft having a distal end;
- an end effector located at the distal end of the shaft, said end effector adapted to receive electrosurgical energy therein, said end effector comprising:
  - first and second elements comprising first and second opposed tissue contacting surfaces respectively, said surfaces moveable relative to each other from an open, spaced-apart position for positioning tissue therebetween, to a closed position for engaging the tissue, at least a portion of one of said surfaces being electrically conductive and arranged to receive the electrosurgical energy;
  - a cutting element moveable to cut tissue engaged by said end effector;
- an actuating device operatively coupled to the cutting element, said actuating device extending through said shaft to said cutting element and arranged to actuate said cutting element to cut tissue; and
- a locking mechanism operatively coupled to said actuating device, said locking mechanism having a first position in which said locking mechanism engages said actuating device to prevent actuation of said cutting element, and a second position in which said locking mechanism releases said actuating device to permit actuation of said cutting element;

clamping tissue between said surfaces;
applying electrosurgical energy to treat said tissue;
determining that tissue treatment is complete;
then moving said locking mechanism from said first position to said second position; and
cutting said tissue with said cutting element.

16. The method of claim 15 further comprising:
measuring the electrical impedance of the tissue to which electrosurgical energy is applied; and
prior to cutting said tissue, indicating to a user of said instrument when the tissue is coagulated to a desired degree.

* * * * *